US 6,568,900 B2

(12) United States Patent
Conrad et al.

(10) Patent No.: US 6,568,900 B2
(45) Date of Patent: May 27, 2003

(54) PRESSURE SWING CONTACTOR FOR THE TREATMENT OF A LIQUID WITH A GAS

(75) Inventors: Wayne Ernest Conrad, Hampton (CA); Helmut Gerhard Conrad, Hampton (CA); Richard Stanley Philips, Courtice (CA)

(73) Assignee: Fantom Technologies Inc., Welland (CA)

( * ) Notice: Subject to any disclaimer, the term of this patent is extended or adjusted under 35 U.S.C. 154(b) by 0 days.

(21) Appl. No.: 09/849,525

(22) Filed: May 7, 2001

(65) Prior Publication Data

US 2002/0027109 A1 Mar. 7, 2002

Related U.S. Application Data

(63) Continuation-in-part of application No. PCT/CA99/10150, filed on Nov. 8, 1999, which is a continuation-in-part of application No. 09/240,615, filed on Feb. 1, 1999, now abandoned, which is a continuation-in-part of application No. 09/240,617, filed on Feb. 1, 1999, which is a continuation-in-part of application No. 09/240,619, filed on Feb. 1, 1999.

(51) Int. Cl.[7] .............................................. F04D 5/00
(52) U.S. Cl. ......................................... 415/90; 415/910
(58) Field of Search ................................ 415/90, 910

(56) References Cited

U.S. PATENT DOCUMENTS

| 2,087,834 A | 7/1937 | Brown et al. ............... 103/115 |
| 2,622,859 A | 12/1952 | Gettins |
| 2,626,135 A | 1/1953 | Serner ........................ 259/106 |
| 3,273,865 A | 9/1966 | White ......................... 259/108 |
| 3,650,632 A | 3/1972 | Shanahan ..................... 415/90 |
| 3,699,776 A | 10/1972 | La Raus ....................... 62/157 |
| 3,751,908 A | 8/1973 | Colwell et al. ............. 60/39.43 |
| 3,772,188 A | 11/1973 | Edwards ....................... 210/15 |
| 3,823,728 A | 7/1974 | Burris ......................... 137/88 |
| 3,837,627 A * | 9/1974 | Sence et al. ............. 210/242.2 |
| 3,856,671 A | 12/1974 | Lee et al. ..................... 210/63 |
| 3,865,721 A | 2/1975 | Kaelin ........................... 210/7 |
| 4,019,986 A | 4/1977 | Burris et al. ................ 210/139 |
| 4,025,225 A | 5/1977 | Durant ......................... 415/90 |
| 4,201,512 A | 5/1980 | Marynowski et al. ......... 415/90 |
| 4,255,081 A * | 3/1981 | Oklejas et al. ............... 415/90 |
| 4,267,052 A | 5/1981 | Chang ......................... 210/629 |
| 4,269,719 A | 5/1981 | Yamamoto .................... 210/803 |
| 4,403,911 A * | 9/1983 | Possell ......................... 415/90 |
| 4,453,953 A | 6/1984 | Tanaka et al. ................ 55/163 |

(List continued on next page.)

FOREIGN PATENT DOCUMENTS

| DE | 27 38 181 A1 | 8/1977 | ............ C02C/1/04 |
| EP | 0 378 994 | 4/1990 | ............ C02F/1/78 |
| GB | 1046363 | 10/1966 | |
| JP | 52115778 | 9/1977 | |
| JP | 54-26280 | 2/1979 | ............ C02C/5/00 |
| JP | 57032789 | 2/1982 | ............ C02F/1/78 |
| JP | 61-185386 | 8/1986 | ............ C02F/1/78 |
| JP | 62213890 | 9/1987 | ............ C02F/1/02 |
| JP | 63-104697 | 5/1988 | |
| JP | 7008976 | 1/1995 | ............ C02F/1/78 |
| JP | 7275873 | 10/1995 | ............ C02F/1/78 |
| JP | 10216752 | 8/1998 | ............ C02F/1/78 |

*Primary Examiner*—Chester T. Barry
(74) *Attorney, Agent, or Firm*—Philip C. Mendes da Costa; Bereskin & Parr (57) ABSTRACT

A residential method for treating water with an oxidizing gas operates under elevated pressure. The elevated pressure is obtained by means of a pressurized oxidizing gas source (eg. an air pump) or a Prandtl layer turbine. The elevated pressure of the treated water is optionally used to dispense the treated water. The Prandtl layer turbine may be used to obtain particularly fine bubbles of a gas (eg. bubbles from about $1\mu$ to about $20\mu$ in diameter) in a liquid.

20 Claims, 6 Drawing Sheets

U.S. PATENT DOCUMENTS

| | | | |
|---|---|---|---|
| 4,534,654 A | 8/1985 | Alt et al. | 366/137 |
| 4,773,819 A | 9/1988 | Gurth | 415/90 |
| 4,902,196 A | 2/1990 | Byrd | 415/90 |
| 4,940,385 A * | 7/1990 | Gurth | 415/206 |
| 5,015,394 A | 5/1991 | McEllhenney et al. | 210/744 |
| 5,041,217 A | 8/1991 | Reid | 210/194 |
| 5,072,780 A | 12/1991 | Yabe | 165/1 |
| 5,147,563 A | 9/1992 | Long, Jr. et al. | 210/758 |
| 5,160,459 A | 11/1992 | Guarnaschelli et al. | 261/92 |
| 5,160,461 A | 11/1992 | Burrows | 261/140.1 |
| 5,174,726 A | 12/1992 | Findlay | 417/205 |
| 5,186,604 A | 2/1993 | Iorio et al. | 415/90 |
| 5,213,718 A * | 5/1993 | Burgess | 210/242.2 |
| 5,213,773 A | 5/1993 | Burris | 422/256 |
| RE34,386 E | 9/1993 | Davidson et al. | 416/242 |
| 5,314,644 A | 5/1994 | Michelsen et al. | 261/84 |
| 5,534,118 A | 7/1996 | McCutchen | 202/205 |
| 5,578,205 A * | 11/1996 | Martin | 210/199 |
| 5,683,576 A | 11/1997 | Olsen | 210/138 |
| 5,709,799 A | 1/1998 | Engelhard | 210/748 |
| 5,713,968 A | 2/1998 | Fruitman et al. | 51/296 |
| 5,730,784 A | 3/1998 | Smith et al. | 95/181 |
| 5,776,351 A | 7/1998 | McGinness et al. | 210/748 |
| 5,800,704 A | 9/1998 | Hansen | 210/169 |
| 5,863,413 A | 1/1999 | Caren et al. | 205/688 |
| 5,868,189 A | 2/1999 | Jarvis | 150/165 |
| 5,971,368 A | 10/1999 | Nelson et al. | 261/64.3 |
| 5,972,714 A | 10/1999 | Roland et al. | 436/135 |
| 6,176,899 B1 * | 1/2001 | Murphy et al. | 95/263 |

\* cited by examiner

PRESSURE SWING CONTACTOR FOR THE TREATMENT OF A LIQUID WITH A GAS

This application is a continuation in part of Application PCT/CA99/10150 filed Nov. 8, 1999 which is a continuation-in-part of U.S. patent application Ser. Nos. 09/240,615 now abandoned; 09/240,617 and 09/240,619 all of which were filed on Feb. 1, 1999.

FIELD OF THE INVENTION

This invention relates of a domestic apparatus for treating a liquid such as water with a gas such as ozone. The apparatus may be used in the production of water suitable for human consumption from water contaminated by one or more of microorganisms, chemicals, heavy metals and minerals. The gas may be present either by itself or in combination with one or more other gasses and/or one or more other liquids associated therewith. Further, the liquid with which the gas is reacted may be present by itself or may also have one or more liquids and/or one or more other gases associated therewith.

BACKGROUND OF THE INVENTION

The production of water suitable for human consumption from water contaminated by one or more of microorganisms, chemicals, heavy metals and minerals is a requirement throughout the world. Many different proposals have been made for the purification of contaminated water.

A popular system in widespread use for the purification of contaminated water is a filtration based system. Such systems use a filter made from a combination of a porous media filter, activated carbon, and an ion exchange resin through which the contaminated water is passed. The filtered water is typically fed into a clean water reservoir. This type of system will reduce the levels of chlorine, lead, and pesticides. However, there are several disadvantages associated with this device.

The first disadvantage of this water purification system is that the structure of the filter provides a breeding ground for microorganisms thereby multiplying the dangers of microorganisms which may be present in very low numbers. Another disadvantage of such a water purification system is that the filter life is not measured and it is possible for the user to employ the filter beyond its useful life. A further disadvantage of such a water purification system is that oils and fuels often present in water drawn from lakes and rivers are not readily removed. Further, these oils and fuels tend to coat the filters and damage their operational life and effectiveness. Some filtration based products now incorporate a means of measuring the water volume passing through the filter and an indicator as to when to change the filter. Other filters incorporate an iodine product to minimize the risk of microbiological hazards, however, these materials often impart undesirable tastes and many are potential carcinogens.

Another popular system in use for the purification of contaminated water is a system which employs ultraviolet light for disinfection in series with a porous media and carbon filter. This type of system will reduce the levels of chlorine, lead, and pesticides and has some disinfection capability. One disadvantage with this system is that the ultraviolet light's disinfection efficacy is greatly diminished by turbidity or colour in the water which can cause the filter to become contaminated by microorganisms which can readily live and breed therein thereby multiplying the danger from any microorganisms which may be present. Thus, the filter of this system also suffers from the disadvantages associated with filters of filtration based systems.

BRIEF SUMMARY OF THE INVENTION

In accordance with the instant invention, there is provided a water treatment apparatus comprising a Prandtl layer turbine having a housing and a plurality of spaced apart members rotatably mounted within the housing; at least one inlet port for introducing a gas comprising at least ozone and water into the housing, the Prandtl layer turbine raising the gas and water to a first pressure; and, a chamber positioned downstream from the Prandtl layer turbine and at a second pressure which is lower than the first pressure.

In one embodiment, the chamber is at a pressure sufficiently low to promote the formation of microbubbles.

In another embodiment, the pressure differential between the first and second pressures is 20 psi or more.

In another embodiment, the pressure differential between the first and second pressures is from about 40 to about 100 psi.

In another embodiment, the apparatus is adapted to be connected upstream of a water supply line in a residence and the chamber comprises a treated water storage chamber and the treated water storage chamber is at a pressure sufficiently high to provide motive force to move the treated water through the water supply line when treated water is required.

In another embodiment, the chamber is configured such that the ozone and water depressurize effectively instantaneous upon entering the chamber.

In accordance with the instant invention, there is also provided a mixing apparatus comprising a housing, at least one inlet port for introducing at least one gas and at least one liquid to the housing; a Prandtl layer turbine mounted within the housing and positioned such that the at least one gas and at least one fluid flow through the Prandtl later turbine and, a chamber positioned downstream from the Prandtl layer turbine and at a lower pressure than the at least one gas and at least one fluid is exposed to in the Prandtl layer turbine whereby the gas forms microbubbles upon exposure to the lower pressure of the chamber.

In one embodiment, the Prandtl layer turbine comprises a plurality of discs and a catalyst reactive with at least one of the gas and the liquid is applied to at least a portion of one of the discs.

In another embodiment, the mixing apparatus further comprises a catalyst reactive with at least one of the gas and the liquid is housed in the chamber.

In another embodiment, the mixing apparatus further comprises a passageway in flow communication with a source of ozone whereby the at least one gas comprises ozone and the at least one liquid comprises water and the mixing apparatus is used in the treatment of water.

In another embodiment, the mixing apparatus further comprises a passageway in flow communication with a source of at least two gases whereby at least two gasses are introduced through the inlet port and the at least one liquid is inert such that the at least one liquid is a media for the dissolution of one of the gases into another of the gases or for the reaction of the gases with each other.

In another embodiment, the mixing apparatus further comprises a catalyst reactive with at least one of the at least one gas and the at least one liquid.

In accordance with the instant invention, there is also provided a mixing apparatus comprising a Prandtl layer means having a housing and disc means rotatably mounted within the housing; means for introducing at least one gas and at least one liquid to the housing; and, means for rapidly depressurizing the gas/liquid mixture whereby microbubbles are produced.

In one embodiment the Prandtl layer means includes a plurality of discs and a catalyst reactive with at least one of the gas and the liquid is applied to at least a portion of one of the discs.

In another embodiment a catalyst reactive with at least one of the gas and the liquid is housed in the means for rapidly depressurizing the gas/liquid mixture.

In another embodiment, the mixing apparatus further comprises a passageway in flow communication with a source of ozone whereby the at least one gas comprises ozone and the at least one liquid comprises water and the mixing apparatus is used in the treatment of water.

In another embodiment, the mixing apparatus further comprises a passageway in flow communication with a source of at least two gases whereby at least two gasses are introduced into the housing and the at least one liquid is inert such that the at least one liquid is a media for the dissolution of one of the gases into another of the gases or for the reaction of the gases with each other In another embodiment the Prandtl layer turbine is driven by a motor.

In another embodiment the Prandtl layer turbine is driven by the fluid flowing through the Prandtl layer turbine.

In accordance with the instant invention, there is also provided a batch method for purifying water with a gas comprising ozone in a sealed vessel comprising the steps of manually introducing water to be treated into the vessel; increasing the pressure in the vessel by supplying pressurized gas to the vessel to obtain treated water; terminating the treatment cycle; and, withdrawing treated water from the vessel.

In one embodiment the vessel has a water inlet and an associated releasable cap and step (a) comprises removing the releasable cap, pouring water to be treated into the vessel through the water inlet and attaching the releasable cap to the water inlet.

In another embodiment, the method a further comprises the step of terminating the treatment cycle when the pressure in the vessel reaches a predetermined level In another embodiment, the method a further comprises the step of reducing the pressure in the vessel prior to withdrawing treated water from the vessel and the treated water is withdrawn from the vessel by removing the releasable cap from the water inlet.

In accordance with the instant invention, there is also provided a method for treating a liquid comprising water in a sealed vessel, with a gas comprising ozone, comprising the steps of introducing the gas into the vessel; increasing the pressure in the vessel; reducing the pressure to promote the formation of microbubbles and obtaining treated water by passing an off gas including ozone through an ozone destructor; and, withdrawing treated water from the vessel.

In one embodiment the pressure is reduced at a rate sufficiently fast to produce microbubbles having a diameter from 1 to 20 microns.

In another embodiment the pressure is reduced in under 2 seconds.

In another embodiment the pressure is increased in step (b) to a pressure above 20 psig.

In another embodiment this method further comprises the step of terminating the treatment cycle when the pressure in the vessel reaches a predetermined level.

In accordance with the instant invention, there is also provided a batch method for treating a liquid comprising water with a gas comprising ozone in a sealed vessel comprising the steps of introducing water to be treated into the vessel; increasing the pressure in the vessel by supplying pressurised gas to the vessel to obtain a water/gas mixture at an elevated pressure; and, terminating the treatment cycle when the pressure in the vessel reaches a predetermined level; and, withdrawing treated water from the vessel.

In one embodiment the method further comprises the step of reducing the pressure to which the water/gas mixture is exposed to form microbubbles In another embodiment the pressure is reduced at a rate sufficiently fast to produce microbubbles.

In another embodiment the microbubbles have a diameter from about 1 to about 20 microns.

In another embodiment the pressure is reduced in under 2 seconds.

In another embodiment the pressure is increased in step (b) to a pressure above 20 psig.

In another embodiment the pressure is rapidly reduced by from about 20 to about 280 psi.

In another embodiment the pressure is rapidly reduced by from about 40 to about 100 psi.

In another embodiment after the pressure reduction step, the water/gas mixture is at a pressure which is sufficient to provide a motive force to move treated water to a downstream location.

In accordance with the instant invention, there is also provided a method for treating a liquid comprising water with a gas comprising ozone comprising the steps of supplying pressurised gas to the water to be treated wherein the gas is at a pressure above the pressure of the water to produce a gas/water mixture at a first pressure; and, rapidly reducing the pressure of the gas/water mixture to obtain the gas/water mixture at a second pressure wherein some of the gas is in the form of microbubbles.

In one embodiment the difference between the first and second pressures is from 20 to 280 psi.

In another embodiment the difference between the first and second pressures is from 40 to 100 psi.

In another embodiment the pressure is reduced at a rate sufficiently fast such that the microbubbles have a diameter from 1 to 20 microns.

In another embodiment the pressure is reduced in under 2 seconds

In another embodiment the second pressure is sufficient to provide a motive force to move water to a downstream location.

In another embodiment the second pressure is above about 40 psi.

In accordance with the instant invention, there is also provided a method for treating a liquid comprising water with a gas comprising ozone comprising the steps of supplying pressurised gas to the water to be treated wherein the gas is at a pressure above the pressure of the water to produce a gas/water mixture at a first pressure; and, reducing the pressure of the gas/water mixture to obtain the gas/water mixture at a second pressure wherein the second pressure is sufficient to provide a motive force to move water to a downstream location.

In one embodiment the difference between the first and second pressures is from 20 to 280 psi.

In another embodiment the difference between the first and second pressures is from 40 to 100 psi.

In another embodiment the pressure is reduced at a rate sufficiently fast such that the microbubbles have a diameter from 1 to 20 microns.

In another embodiment the pressure is reduced in under 2 seconds,

In another embodiment the second pressure is above about 40 psi.

BRIEF DESCRIPTION OF THE DRAWINGS

A further, detailed description of the invention, briefly described above, will follow by reference to the following drawings of a preferred embodiment of the invention in which.

DETAILED DESCRIPTION OF THE PREFERRED EMBODIMENT

In one preferred embodiment, the apparatus is for use in a domestic (i.e. residential) environment, eg. a house or a cottage, and the water to be treated may be from a municipal water supply which is fed to a house through supply pipes. It may also be water which is obtained from a well maintained by the individual or any other source that the individual has for their house, cottage RV or the like. Thus, the apparatus may be used in various domestic applications, such as a counter top water purifier, a point of entry or point of use (under counter) water purifier. Further, it may be used as a portable water purifier.

The liquid is treated in a container 1. Container 1 may be of any particular design that will allow the pressure exerted on the liquid being treated therein to be increased. The liquid and the gas may be introduced into the container by any method known in the art. For example, container 1 may have a inlet port for the liquid to be treated and a separate inlet port for the gas to treat the liquid. Alternately, the liquid and the gas may be introduced through the same inlet port. While some of the gas may be introduced into container 1 when at least some of the liquid is in container 1, it is preferred that all of the gas is introduced into container 1 once a full charge of liquid to be treated has been introduced into container 1.

The apparatus is designed to permit pressure to build up in container 1 during use. The pressure in container 1 may be increased by the introduction of the fluids into container 1. Preferably, the pressure is increased at least in part by the introduction of gas into container 1, e.g by a gas pump, when container 1 has already been provided with at least part of charge of the liquid to be treated. More preferably, the pressure is increased by the introduction of gas into container 1 when container 1 has already been provided with a full charge of the liquid to be treated.

Figure 1:
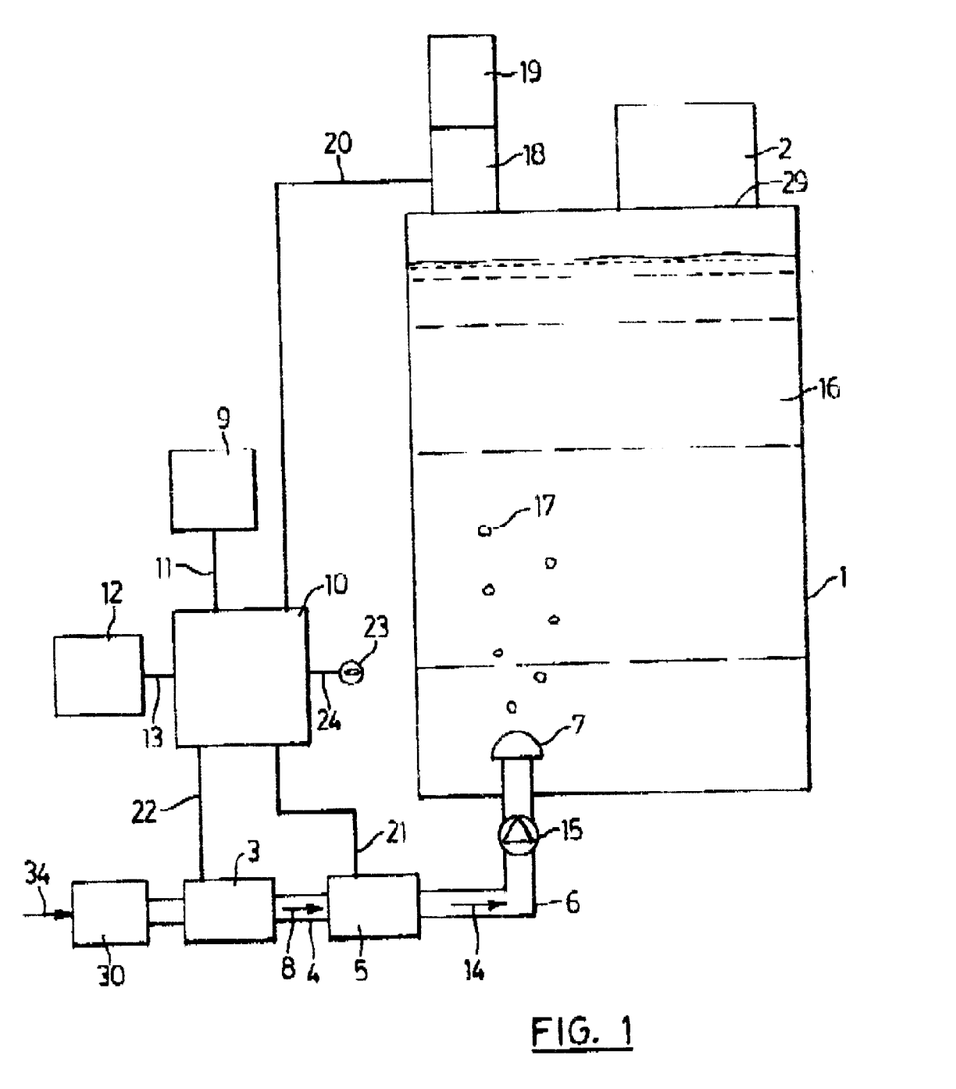
FIG. 1 shows a schematic representation of the apparatus according to the instant invention.

FIG. 1 schematically illustrates a system for efficiently dissolving ozone in water and subsequently causing microbubble formation to disinfect the water and oxidize pollutants present. While the system will be described herein in relation to the use of ozone to treat water, it will be appreciated that it may also readily be modified for use with any system wherein at least one gas is used to treat at least one liquid.

Water 16 is introduced into container 1 through liquid inlet port 29. Liquid inlet port 29 May be supplied by a hose. Alternately, liquid inlet port 29 may comprise an opening through which water may be poured such as from a jug, faucet or the like. Liquid inlet port 29 is sealable so as to allow pressure to build up in container 1 during the treatment of water 16. As shown in FIG. 1, liquid inlet port 29 may receive a resealable cap 2. The cap 2 may be removably affixed to container 1 by any means, such as by a screw thread or a bayonet mount. When the cap is closed, the container is sealed.

Figure 2:
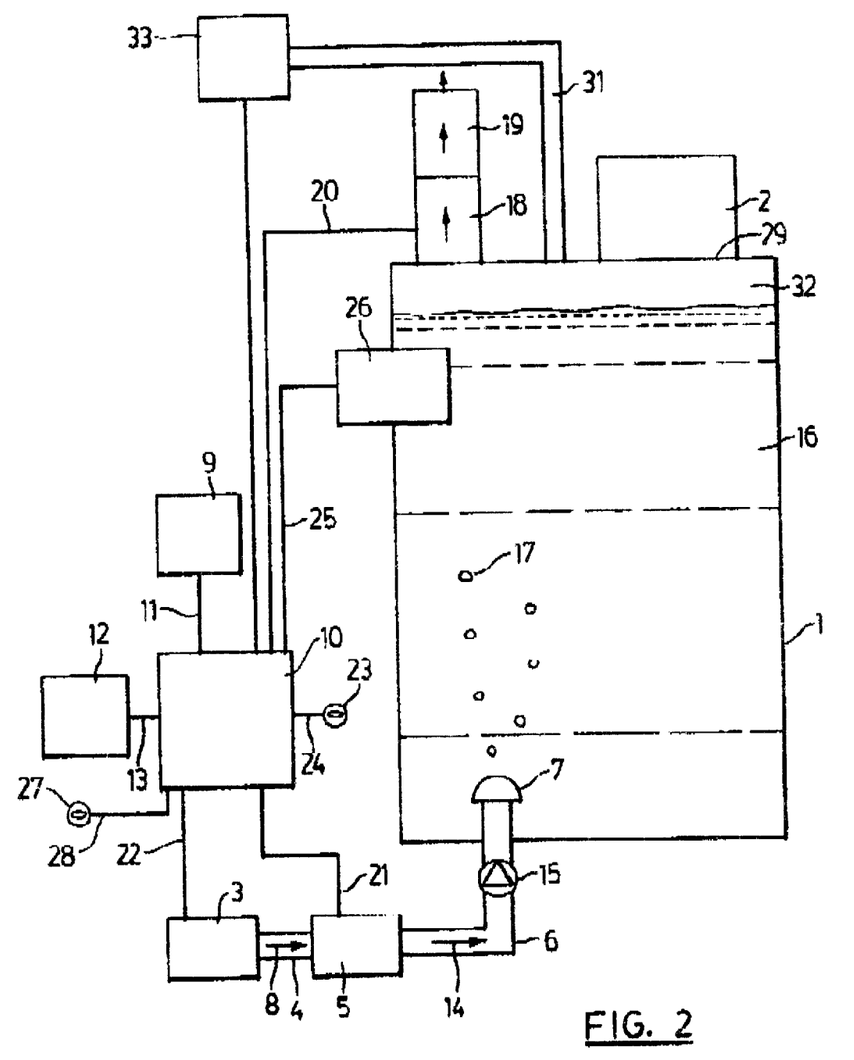
FIG. 2 shows a schematic representation of an alternate apparatus according to the instant invention.

It will be appreciated that container 1 may allow some fluid to escape there from during the treatment of water 16 (eg. some of the treatment gas may exit container 1 during the treatment) In such an embodiment, liquid inlet port 29 may only be partially sealed. For example, as shown in FIG. 2, a bleed stream 31 of off gas may be fed to sensor 33 to monitor the progress of the treatment cycle. Preferably all of the fluid is maintained in container 1 until the treatment cycle is completed and accordingly liquid inlet port 2 is preferably fully sealable.

The control circuit of this device derives power from any power source, for example, a battery 12 by means of wire 13. The power source could also be, for example, an electrical outlet. A user may then activate the unit by pushing start button 9 which sends a signal to the controller 10 through the wire 11. The unit may be actuated by any other means known in the art. For example, the unit may be actuated when cap 2 is sealed or, if the water is supplied via a hose, when a sensor (eg. a float switch) detects a full charge in container 1.

The unit is provided with a source of ozone. This may be a canister of compressed ozone gas which is provided as part of the unit or fed to container 1 via a hose (not shown). Preferably, the device includes an ozone generator and the ozone generator is supplied with a source of oxygen. This source of oxygen may be the ambient air. Preferably, oxygen enriched air is used. Accordingly, the unit may be connected to a source of oxygen enriched air for example the unit may be provided with a canister of compressed gas containing elevated levels of oxygen or pure oxygen, or it may be connected via a hose to such a source or, preferably, the unit may include an oxygen concentrator, such as those which utilize pressure swing adsorption and are known in the art. Pressurized air may be provided to an oxygen concentrator such as by a motor driven fan, or any other manner known in the art (not shown).

Figure 3:
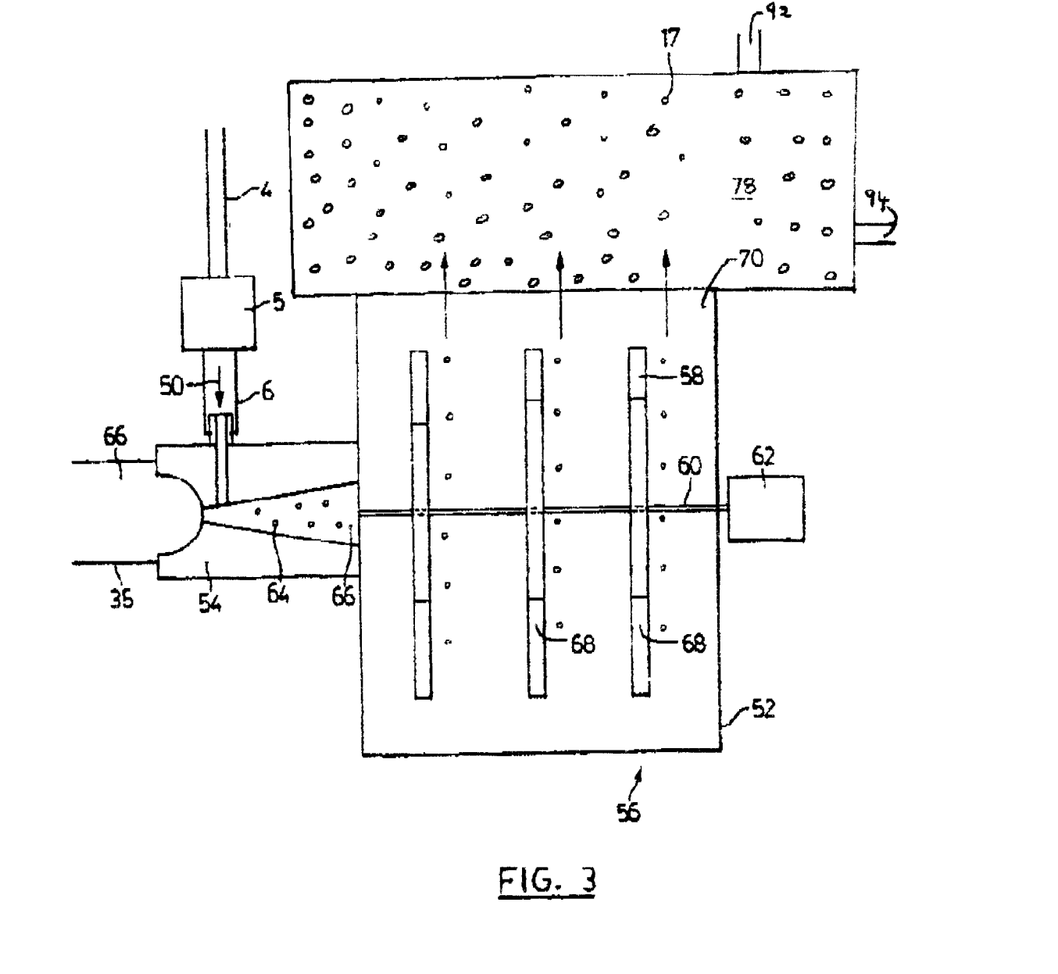
FIG. 3 is a schematic representation or a mixing vessel that may be used in the embodiments or FIGS. 1 and 2.

The apparatus includes means for increasing the pressure in the treatment vessel. In the embodiment of FIG. 1, this means comprises air pump 30. Air stream 34 (eg. ambient air) is fed to air pump 30. In the embodiment of FIG. 3, this means comprises Prandtl layer turbine 56. Any pressurization means known in the art may be used (eg. a water pump through which water 16 and ozone oxygen mixture 14 are fed to container 1).

When the unit is actuated (eg. when start button 9 is pushed), ozone is fed to container 1. If the device includes an ozone generator as shown in FIG. 1, then the control circuit provides power to the oxygen gas source 3 (eg. an oxygen concentrator) and to the ozone generator 5 through wires 21 and 22, respectively.

The oxygen gas source 3 provides gas containing oxygen which is preferably at an elevated pressure (eg. 30 psi). If the gas 8 is at an insufficient pressure, then a pump may be provided at any point prior to the entry of the gas into container 1 to boost the pressure of the gas as it enters container 1. Gas 8 then flows from the oxygen rich gas source 3 through tube 4 and into the ozone generator 5 where at least a portion of the oxygen present is converted to ozone. This ozone oxygen mixture 14 generated by the ozone generator then flows through the pipe 6, through the one way check valve 15 and into the water 16 through, eg., sparger 7 which serves to disperse the gas in the water 16 in the form of into fine bubbles or microbubbles 17 (eg. having a diameter from about $50\mu$ to about $100\mu$ and preferably less). Other means may be used to introduce mixture 14 into container 1 so as to form a stream of bubbles including venturis and the use of a Prandtl layer turbine.

A Prandtl layer turbine may be used to mix the ozone with some of the water which may then be fed to container 1. Various embodiments of Prandtl layer turbines have been developed over the years. Prandtl layer turbines comprise a plurality of rotatably mounted members (generally in the form of flat discs which are typically relatively thin) which are rotatably mounted in a housing. These devices are described in the U.S. Pat. No. 1,061,206 (Tesla). The method and apparatus of the instant invention is applicable to all designs of a Prandtl layer turbine.

Referring to FIG. 3, water 16 (from feed tube 35) and ozone containing gas 50 are introduced into a housing 52, for example, by being drawn through a venturi 54 by means of a Prandtl layer turbine 56. The Prandtl layer turbine 56 consists of a series of plates (preferably discs) 58 which are non-rotatably mounted to a shaft 60 which is itself rotatably mounted in housing 52 such as by being connected to a motor 62 which provides the motive force to rotate the plates 58. The rotation of the plates 58 causes the fluid to be drawn through the venturi 54 which in turn causes gas 50 to be drawn from the hose 14 into the venturi 54. It will further be appreciated that the gases and the liquids may be separately introduced into Prandtl layer turbine 56.

Gas 50 and water 16 are preferably mixed prior to their introduction into Prandtl layer turbine 56. More preferably, the gas 50 is preferably mixed with water 16 in such a manner as to form small gas bubbles 64 in the fluid flow stream. The bubbles may vary in size from about 50 to about 250 microns in diameter, more preferably from about 50 to about 100 and, most preferably, 50 to about 75. It will further be appreciated that various other devices besides venturi 54 may be used to create bubbles 64, such as a sparger. By creating a plurality of small gas bubbles 64 which are introduced into Prandtl layer turbine 56, the surface area of gas 50 in water 16 which is introduced into Prandtl layer turbine 56 is increased thereby increasing the dissolution which may be achieved of gas 50 into water 16 in Prandtl layer turbine 56.

The gas laden fluid stream 66 is drawn through venturi 54 and into the spaced apart plates 58 such as via openings 68 in plates 58. As the fluid is forced outwards on a radial serpentine path along the rotating plates 58 the pressure of the fluid increases thereby increasing the dissolution of the gas 50 into water 16. This increase in the pressure of the fluid is possible because, unlike conventional vane or centrifugal pumps, plates 58 in Prandtl layer turbine 56 will not be cavitated by the presence of the gas. The Prandtl layer turbine may create a force of, for example up to 100 psig and, more preferably up to 250 psig. The fluid with the gas dissolved therein may be sent to other apparatus for further processing.

Figure 4:
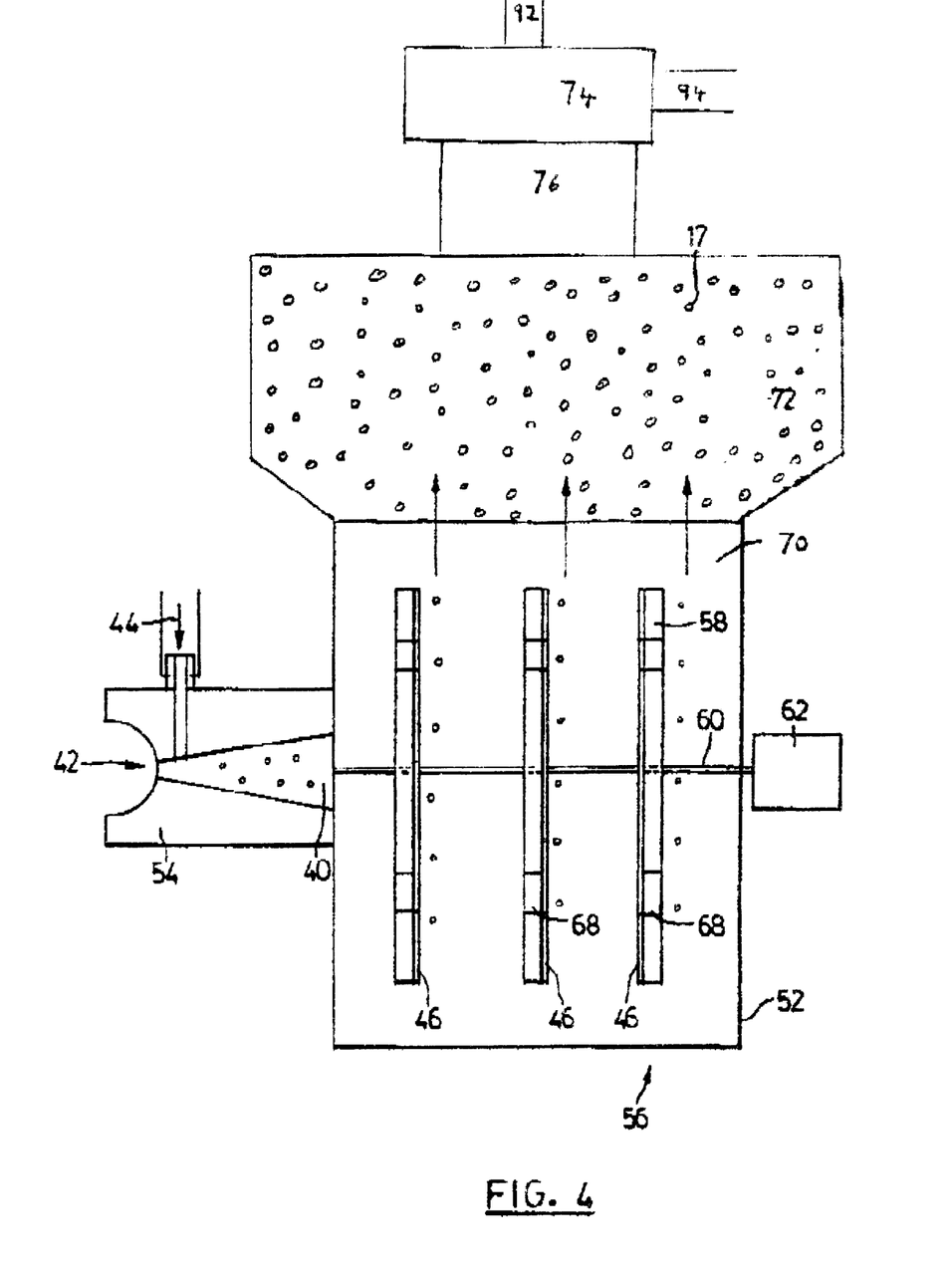
FIG. 4 shows a schematic representation of an alternate apparatus to that of FIG. 3.
Figure 5:
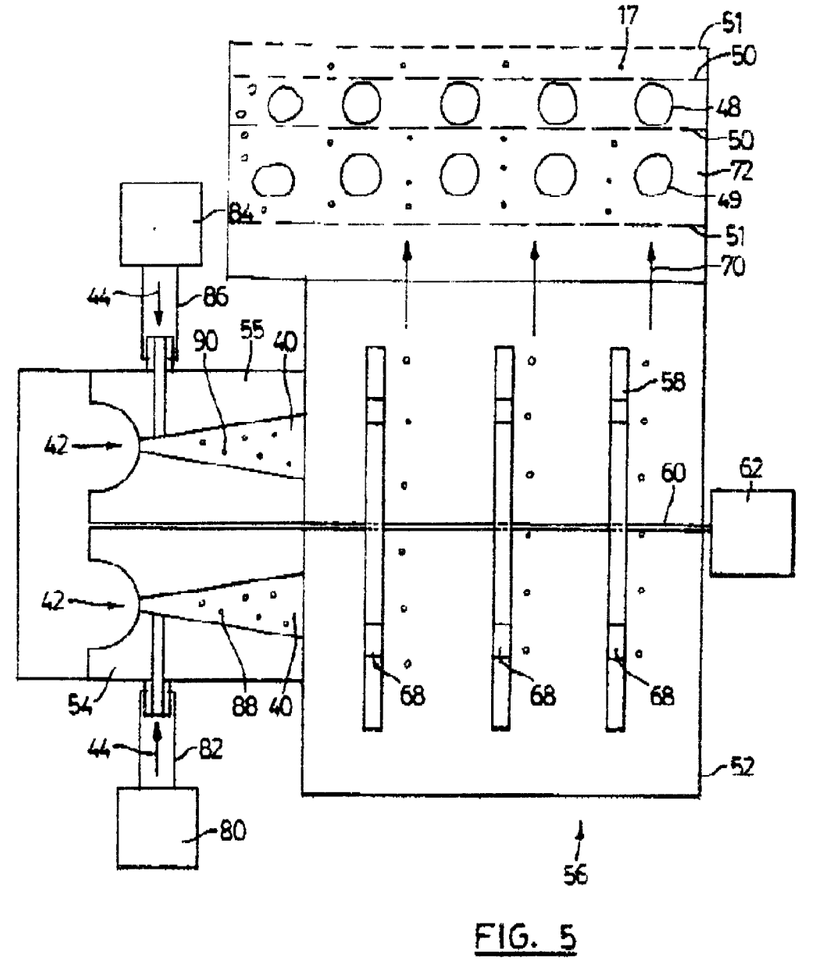
FIG. 5 shows a schematic representation of a further alternate apparatus to that of FIG. 3; and, FIG. 6 shows a schematic representation of an alternate apparatus according to the instant invention.

Alternately, the pressurized liquid mixture 70 may then be subjected to a reduced pressure. For example, the pressurized gas and liquid mixture 70 may be passed into an expansion zone 72 (which may be a chamber downstream from the Prandtl layer turbine such as container 1) wherein the pressure to which the gas and liquid mixture 70 is subjected is reduced and preferably rapidly reduced. Container 1 may already be at a reduced pressure so that the pressure reduction occurs upon the mixture entering container 1. This may be achieved by increasing the cross sectional area of the downstream passage, by use of a pressure reduction valve, by means of a throttling orifice of the like. For example, storage chamber 78 has a greater cross sectional area than that of the Prandtl layer turbine exit (see FIG. 3). The cross sectional area may increase step wise as shown in FIGS. 3 and 5 or incrementally as shown in FIG. 4. Expansion zone 72 may also have a downstream end exposed to a lower pressure (which could be the ambient but could be still be at a pressure greater than atmospheric pressure but lower than the pressure produced by the Prandtl layer turbine). Due to the length of expansion zone 72, the pressurized gas and liquid mixture 70 produces microbubbles as it passes through the expansion zone.

Alternately, mixture 70 may be fed to container 1 at an elevated pressure and the pressure reduced once mixture 70 has been fed to container 1. For example, mixture 70 may be fed to container 1 and the pressure is partially or fully reduced to allow microbubbles to form. This could be achieved by opening a pressure relief valve or opening the top of container 1. A sensor may be used to monitor the treatment of the water and when the water is treated to a desired level of purity, the pressure in container 1 may be further reduced. Alternately, the elevated pressure may be used to dispense the treated water.

The liquid/gas mixture in the expansion zone may be at a pressure of, for example, 30–60 psig or even higher, depending upon the pressure developed by the Prandtl layer turbine. This depressurization occurs rapidly, preferably in under 2 seconds, more preferably in under 1 second and, most preferably, is effectively instantaneous upon the liquid/gas mixture entering expansion zone 72. This, depressurization allows the dissolved gas to come out of solution to form a suspension of ultra-fine bubbles 17. The babbles may vary in size from about 1 $\mu$ to about 100 $\mu$, preferably from 1 $\mu$ to about 50 $\mu$ in diameter, more preferably from about 1 micron to about 20 $\mu$ and, most preferably, from 1$\mu$ to 5 $\mu$. Due to the relatively fine nature of the bubbles, a large increase in the surface area of the gas is achieved. If the pressure reduction is conducted so as to achieve bubbles which are a few microns in diameter, then the number of bubbles which are achieved may be sufficiently high such that mixture 70 becomes translucent and, preferably, opaque. By varying the rate of pressure reduction and the amount of the pressure reduction, the size and the number of the bubbles may be adjusted. Generally the pressure reduction experience during the rapid depressurization is at least about 20 psi. The greater the pressure drop, the smaller the bubbles which will be formed.

The reduced pressure mixture 70 may be used for various purposes. As shown in FIG. 3, the reduce pressure mixture comprises ozone and water. In such a case, the ozone may be used to oxidize contaminants in the water such as pesticides, herbicides, organic contaminants as well as bacteria and viruses. Thus, treated water may be obtained by passing water and an oxidizing gas such as ozone through the Prandtl layer turbine whereby the ozone is intamintley mixed with the water to render the water potable.

The water may then be passed through gas liquid separator 74 which is connected downstream from the expansion zone in flow communication with Prandtl layer turbine by passage 76 (see FIG. 4) The off gas exit via, e.g. passage 92 and the water exits, e.g. via passage 94. Alternately, the expansion zone may be a storage vessel 78 whereby ozone and other gasses mixed in with the water may rise to the top of the tank leaving treated water available for use. In a further alternate embodiment, storage vessel 78 is positioned downstream from gas liquid separator 74.

If the Prandtl layer turbine forms part of a water treatment apparatus for a house, such as a whole house unit (i.e. to treat all or most of the water as it enters a residential dwelling) or a point of use unit (i.e. a unit positioned upstream of a bathroom, sink or the like to treat water for that area of a dwelling), then the water which is fed to the unit is under pressure (typically about 60 psi in North America). A Prandtl layer turbine can raise the pressure of the mixture which flows there through up to 300 psi. Therefore, while the expansion zone is at a pressure less than the pressure in the Prandtl layer zone, it may be at a pressure sufficiently high to provide the motive force (e.g. water pressure) to drive the treated water to flow through the plumbing in the residence (e.g. downstream from storage vessel 78 in FIG. 3 or passage 94 in FIG. 4) when a tap or the like is turned on. Preferably, the pressure differential between pressure in the Prandtl layer turbine and the expansion zone is at least 20 psi. However, the pressure differential may be about 60–80 psi or more and may be up to 100 psi or more. Thus the pressure differential may be from about 20 to about 280 psi, preferably front about 40 to about 100 psi and more preferably about 60 to about 80 psi. Preferably, the expansion zone or chamber is at a pressure about equal to the line pressure to the residence. For example, the pressure may be at about 60 psi, However, in some instances, a pressure of about 40 psi may supply sufficient motive force. In this way, a water treatment apparatus may be retrofitted into a residence without a perceptible change in the water pressure in the residence.

In an alternate embodiment, the reduced pressure mixture may be used for treating another material (in such a case, water 16 may be any fluid which functions as an inert carrier). An example of this could be the use of the reduced pressure mixture 70 as a treatment agent. For example, once again, if gas 50 included an oxidation agent (eg. ozone or peroxide), then the reduced pressure mixture may be fed to a tank containing a material (eg. a chemical compound such as a pesticide, a herbicide or metal) which is to be oxidized. In such a case, the apparatus may be used not to produce drinking water but to permit the safe disposal of toxic material.

It will also be appreciated that two or more gases may be fed into Prandtl layer turbine 56. The gases may be reactive with each other and water 16 (or any other carrier fluid) may optionally be inert. In such a case, the creation of the microbubbles creates an environment in which the gases may intimately mix and react with each other. It will be appreciated by those skilled in the art that other variations of the fluids which are introduced into Prandtl layer turbine 56 may be used and that the reduced pressure mixture may be used for various purposes including from polishing a surface for electroplating operations.

It will further be appreciated that a catalyst may be added to the system as shown in FIGS. 4 and 5. If one member of fluid stream 40 is to react with another portion of fluid stream 40 (e.g it may be added via streams 42 and/or 44), then the catalyst may be provided to enhance the reaction.

The catalyst may be added to the system with fluid stream 40 or, alternately, it may be contained within turbine 56 or expansion zone 72. For example, the catalyst may be in the form of a solid, liquid or a gas and accordingly introduced with either or both of gas 44 or fluid 42. Preferably, the catalyst is in the form of a liquid or a solid. The catalyst may be introduced with fluid 40 via venturi 54 or it may be introduced via a separate port into turbine 56. Plates 58 rotate so as to create a Prandtl layer there adjacent. This Prandtl layer creates a zone which effectively prevents solid particles from contacting plates 58. Accordingly, a Prandtl layer turbine is particularly well adapted for receiving particulate matter, such as catalyst particles. By providing the catalyst as part of fluid stream 40, the catalyst is available for transportation downstream with mixture 70.

It will be appreciated that if the catalyst is used to catalyze the reaction between members of fluid stream 40 (as opposed to a reaction involving a material positioned downstream of the apparatus) then the catalyst may be provided in various parts of turbine 56. For example, a catalyst layer 46 may be applied to the surface of plates 58 so as to enhance the reaction of constituents of fluid stream 40 with each other (see FIG. 4). Alternately, or in addition, the catalyst may be provided an expansion zone 72. Referring to FIG. 5, a catalyst may be placed as discreet particles 48 which are sufficiently large so as to be maintained in expansion zone 72 as mixture 70 passes there through. For example, expansion zone 12 may be provided with a pair of opposed mesh screens 50 with catalyst particles 48 positioned there between. Catalyst particles 48 and the openings in mesh 50 are sized so as to maintain catalyst particles in a fixed position in expansion zone 72. Alternately, the catalyst particle may be free floating in expansion zone 12. For example, the entry port and exit port to expansion zone 72 may be provided with mesh screens 51 and catalyst 49 may be positioned between screens 51 so as to be able to travel freely with expansion zone 72.

It will be appreciated that if fluid stream 66 is under a sufficiently great pressure as it enters parental layer turbine 56, that the fluid may assist motor 62 in rotating discs 58 or, alternately, turbine 56 may not include a motor 62 and, instead, fluid stream 66 may comprise the necessary motive force to cause plates 58 to rotate. Preferably, plates 58 rotate at an rpm from about 3000 to about 8000, more preferably from about 3000 to about 5000 and, most preferably, from about 3000 to about 4000. Thus, the spaced apart plates or discs 58 may be driven by the fluid so as to act as a turbine. Alternately, they may be rotated by an external drive member such as motor 62 so as to operate as a pump. Herein, either means of operation is referred to as a "Prandtl layer turbine" for convenience.

In the embodiment shown in FIG. 5, fluid 42 is drawn through venturi 54 and second venturi 55 by means of a Prandtl layer turbine 56. The rotation of the plates 58 causes fluid 42 to be drawn through venturi 54 and through venturi 55. This in turn causes the gas 44 to be drawn from the gas source 80 through tube 82 and into the venturi 54 and also causes gas to be drawn from the gas source 84 through the tube means 86 and into the venturi 55. The gases are preferably drawn into the fluid 42 in such a manner to form small gas bubbles 88 and 90 to form in the respective streams of the fluid 42 which may be introduced separately into Prandtl layer turbine 56.

In the preferred embodiment of FIG. 1, when resealable cap 2 is closed the entry of mixture 14 into container 1 increases the pressure in container 1 thereby increasing the amount of gas which will dissolve into the water 16. When the pressure within the container 1 reaches a given pressure (eg. 200 psi) which may be predetermined, the treatment cycle may terminated by sending a signal to shut off the supply of gas (mixture 14) to container 1. The pressurized fluid may be allowed to stand in container 1 for an extended period of time. Some of the pressure may be released so as to form microbubbles (i.e. at least about 20 psi and preferably more than 40 psi) When it is desired to empty container 1 (eg. it is desired to use the water) the remaining pressure container 1 may be released and water is dispensed. The unit may include a pressure relief valve and pressure switch 18 which causes the container 1 to be automatically vented to the atmosphere through, for example, an ozone off gas destructor 19 when a predetermined pressure is achieved. At this point, a signal may optionally be sent to the controller 10 through wire 20 indicating that a cycle has been completed thus shutting of the supply of mixture 14 to container 1.

A single charge of water 16 in container 1 may be treated by being exposed to the pressurized gas only once or multiple times. When the endpoint of the process is reached (water 16 has been subjected to the desired number of cycles), the controller 10 may turn off the power to the oxygen rich gas source 3 and to the ozone generator 5 through wires 21 and 22 and signal the user that the process is complete, such as by providing power to the green light 23 by means of wire 24

Once the water in container 1 is sufficiently treated, cap 2 may be removed, and the water may be removed for use (eg. it may be poured out of container 1). It will of course be appreciated that the water outlet may be a pipe which is connected to a filter and a dispenser positioned downstream from container 1. A water pump may be included to remove the water and pass it through such a filter. Preferably, the elevated pressure of the ozonation (eg from air pump 30) is used to dispense, or at least assist in dispensing, the treated water).

An alternate embodiment is shown in FIG. 2. In FIG. 2, reference numerals common with those in FIG. 1 are for like features, and are not described again in detail. In this embodiment, container 1 includes a sensor for monitoring the treatment of the water and sending a signal to controller 10 when the treatment is complete. The sensor may send a signal indicating that the treatment was successfully completed or that the treatment was not successfully completed. The sensor may be any of those known in the art. The specific type of sensor will vary depending upon the liquid being treated in container 1. If the liquid is water, the sensor may be an oxygen reduction potential sensor 26 (i.e. an ORP sensor). The ORP sensor 26 monitors the ORP level and transmits it to the controller 10 through a wire 25. The controller monitors the redox level to determine the endpoint of the water treatment process.

For example, if a preset redox level is maintained for a prescribed time, the desired endpoint is reached and the controller 10 signals to the user that the treatment process is complete by providing power to green light 23 by means of wire 24. If a suitable redox level is not achieved and preferably maintained for a prescribed time, and a preset time elapses, the treatment is ended and the water is not suitable for consumption. In this circumstance, the controller 10 may signal that the process is complete but the water is unsuitable for use by providing power to the red light 27 by means of wire 28.

Alternately, if a suitable redox level is not achieved and maintained for a prescribed time, and a preset time elapses, then controller 10 may cause water 16 to be subjected to one or more treatment cycles until either sensor 26 signals that the treatment is successfully concluded or a preset number of cycles are conducted without success.

It will be appreciated that various mechanisms may be used to determine the end point of a treatment cycle. It will also be appreciated that the apparatus need not include a sensor but may be operated on a different basis (eg. it may be run by a timer). At the end of each cycle, sensor 26 or the timer may send a signal, eg. through controller 10, to pressure relief valve and pressure switch 18 to cause container 1 to be vented to the atmosphere.

In an alternate embodiment also shown in FIG. 2, the unreacted gas in a bleed stream of off-gasses 31 from head space 32 is treated to produce a signal which may then be read by ozone sensor 33. Ozone sensor preferably uses an ozone destructor and may double as destructor 19. Such a sensor may operate on various principles.

For example, the signal may be in the form of a temperature change in the off-gas stream. This may be achieved, for example, by subjecting the unreacted gas to a chemical reaction in a reaction zone containing a catalyst to produce heat. In the application of treating water to produce ozone, the sensor contains a catalyst (eg. one or more of manganese dioxide, titanium dioxide, iron oxide, or carbon) for converting ozone to oxygen which produces heat as a by-product. The sensor also includes a temperature sensor, eg. a thermistor, positioned upstream of the catalyst to measure the temperature of the untreated bleed stream and a temperature sensor, eg. a thermistor, to measure the temperature of the treated bleed stream. The temperature difference is proportional to the amount of ozone converted to oxygen and therefore to the concentration of ozone in head space 32. Sensor 33 will provide a reading of the ozone concentration in the head space by measuring the concentration in the bleed stream and, based on the flow rate into the treatment vessel and the flow rate of the bleed stream, this may be used to calculate the total amount of ozone to which the water was exposed.

By measuring the conversion of ozone to oxygen in sensor 33, great flexibility is obtained in the operation of the treatment cycle. For example, as the volume of water and the anticipated level of contaminants in the water can be predetermined, it is possible to calculate the amount of ozone that will be required to treat the water and to program this information into controller 10. The treatment of the water by ozonation may continue until a predetermined total amount of ozone passes through the water 16 and a portion thereof is converted to oxygen in sensor 33. The predetermined amount of ozone may be measured by the difference in resistance between the two temperature sensors and the time during which the temperature difference is measured.

Figure 6:
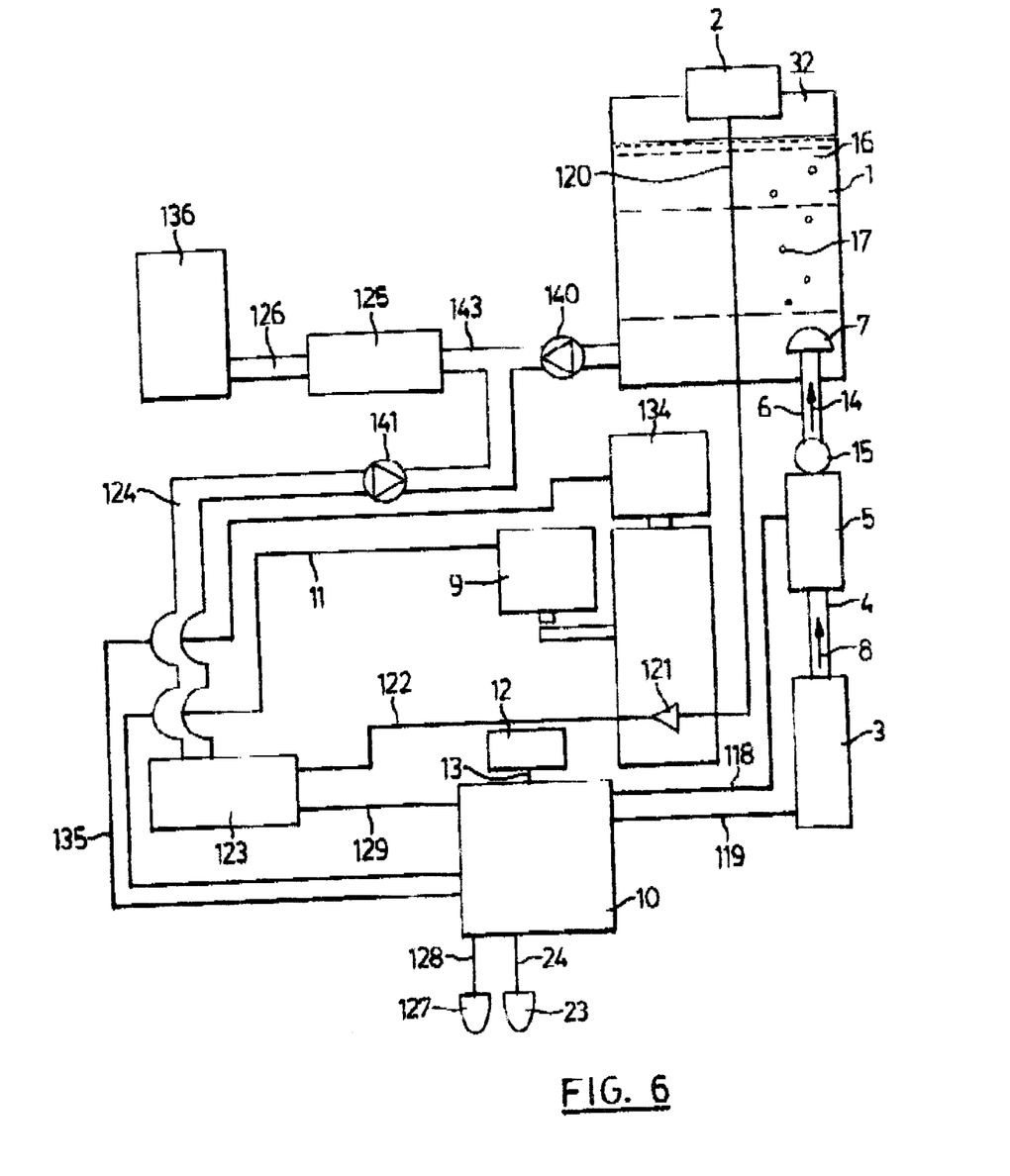

In the embodiment of FIG. 6, the elevated pressure in container 1 is used to dispense the treated water. This embodiment also demonstrates the use of an off gas sensor to control the water treatment cycle.

After passing through the water 16 in the container 1, the gas exits the container 1 through a vent line 120. This removes gas from the head space 32 in container 1 and prevents pressure from building up in the container 1. The vented gas passes through the off gas flow control valve 121 and through tube 122, and into the ozone off gas sensor 123. It then passes through pipe 124, and check valve 41 into tube 43. The vented gas then enters filter 125 and into a treated water vessel (eg a removable carafe) 136 via tube 126 from where it may pass into the room as oxygen rich gas. Thus, the ozone off gas may serve to disinfect the filter 125 and prevent microbiological growth within the filter. Filter 125 may be any filter known in the water filtration art. Preferably, filter 125 comprises carbon block filter.

It will be appreciated that it container 1 is at least partially sealed, eg. valve 121 is closed or at least partially closed, that pressure will build up in container 1. The increase in pressure in container 1 is beneficial in the treatment of water 16 by mixture 14. In such a case, a bleed stream of the off gases may be passed to sensor 123. Alternately, once the pressure has built up to a desired level in container 1 a steady flow of off gasses may be removed from container 1 to prevent further pressure build up in container 1.

Signals from the ozone sensor 123 are transmitted to the control circuit by any means, for example a wire 129. The control circuit 4 monitors the ozone off gas concentration by means of sensor 123.

Ozone sensor 123 measures the level of ozone in the off gas by any of those known in the art. The ozone level may be measured on an intermittent basis as water 16 is treated but is preferably continuously monitored.

Once sensor 123 detects a value representing the successful completion of the water treatment process, controller 10 detects this and may then shut down the power to the power on light 127 by means of wire 128, the power to the oxygen rich gas source 3 by means of wire 119, and the power to the ozone generator by means of wire 118. It may also cause the water ready light 23 to be illuminated by means of wire 24. Depressing the water dispense button 134 will send a signal to the controller 10 by means of wire 135 and will cause the treated water to be decanted from container 1. Preferably, the water is filtered, such as passing it through a filter 125. This may be achieved by a pump (not shown) or other means known in the art.

In the preferred embodiment of FIG. 1, a sufficient amount of pressure is built up in container 1 to cause the water to exit container 1 and to flow through filter 125. To this end, if the treatment cycle is successfully completed, depressing the water dispense button 134 may send a signal to the controller 10 by means of wire 135 which causes the off gas flow control valve 121 to at least partially close, preferably fully close, such as by a mechanical member. Gas, such as from oxygen rich gas source 5, is fed to container 1. This in turn causes pressure to build up within the container 1. When the pressure reaches a preset level (eg. a sufficient amount to cause all of the water in container 1 to pass through filter 125), the water is decanted. In the preferred embodiment, this is achieved by placing a valve 140 which opens at the preset pressure in container 1. Thus the treated water in container 1 will be decanted when the required pressure is reached in container 1. Valve 40 may be a spring loaded check valve. The spring loaded check valve is in communication with the container 1 and the treated water carafe 136. When the check valve is opened, the treated water will flow from the container 1 through tube 143 and through the filter 125 and into the treated water carafe 136 However, it will be appreciated that container 1 may include a pressure sensor which signals controller 10 when the preset pressure is reached and controller 10 may then send a signal to open valve 140. Further, if gas is supplied to container 1 during the dispensing operation, the preset level may be sufficient, together with the supplement gas introduced into container 1 during the dispensing operation, to cause the treated water to pass through filter 125.

In a further embodiment, if the user depresses the dispense button during the delivery of water to the treated water carafe 136 or optionally during the treatment of water 16 in container 1, their another signal is preferably also sent to the controller 10 by means of wire 135. However, since the water treatment is not complete in this case, as a safety feature, the input will cause the off gas flow control valve 121 to be mechanically opened and the oxygen rich gas source 5 to lose power through wire 118 thereby interrupting the dispensing or treatment process. The user may then empty and refill container 1 for another treatment cycle.

Alternately, once a preset amount of time has elapsed during the dispense cycle, the controller 10 may interrupt the flow of gas to container 1 (eg power to the oxygen rich gas source 5 through wire 118 may be terminated) thereby ending the dispensing process. When the user depresses start button 9 in the future, the mechanical off gas flow control valve 121 will be reset to the starting (eg. open) position for the next cycle to proceed.

It will be appreciated by those skilled in the art that various modifications may be made within the spirit of the present invention, the scope of which is limited only by the claims. For example, a different visual signal may be provided to the user to signal the successful of unsuccessful treatment of the water, and/or an audio signal may be provided.

We claim:

1. A water treatment apparatus comprising:
    (a) a Prandtl layer pump having a housing;
    (b) at least one inlet port for introducing a gas comprising at least ozone and water into the housing, the Prandtl layer pump raising the gas and water to a first pressure;
    (c) a chamber positioned downstream from the Prandtl layer pump, the chamber receiving ozonated water from the Prandtl layer pump; and,
    (d) wherein the chamber is at a second pressure which is lower than the first pressure and the pressure differential between the first and second pressures is 20 psi or more.

2. The water treatment apparatus as claimed in claim 1 wherein the chamber is at a pressure sufficiently low to promote the formation of microbubbles.

3. The water treatment apparatus as claimed in claim 1 wherein the chamber is at a second pressure which is lower than the first pressure and the pressure differential between the first and second pressures is from about 40 to about 100 psi.

4. The water treatment apparatus as claimed in claim 1 wherein the apparatus is adapted to be connected upstream of a water supply line in a residence and the chamber comprises a treated water storage chamber and the treated water storage chamber is at a pressure sufficiently high to provide motive force to move the treated water through the water supply line when treated water is required.

5. The water treatment apparatus as claimed in claim 1 wherein the chamber is configured such that the ozone and water depressurize effectively instantaneous upon entering the chamber.

6. The water treatment apparatus as claimed in claim 1 wherein the chamber comprises a treated water storage reservoir.

7. The water treatment apparatus as claimed in claim 6 wherein the chamber is at a pressure sufficiently low to promote the formation of microbubbles.

8. The water treatment apparatus as claimed in claim 7 wherein the chamber is adapted to be connected upstream of a water supply line in a residence and the treated water storage chamber is at a pressure sufficiently high to provide motive force to move the treated water through the water supply line when treated water is required.

9. The water treatment apparatus as claimed in claim 1 further comprising a catalyst reactive with the ozone is housed in the chamber.

10. A mixing apparatus comprising:
   (a) a housing;
   (b) at least one inlet port for introducing at least one gas and at least one liquid to the housing;
   (c) a Prandtl layer pump mounted within the housing and positioned such that the at least one gas and at least one fluid flow through the Prandtl layer pump;
   (d) a chamber positioned downstream from the Prandtl layer pump and at a lower pressure than the at least one gas and at least one fluid is exposed to in the Prandtl layer pump; and,
   (e) a passageway in flow communication with a source of at least two gases whereby at least two gasses are introduced through the inlet port and the at least one liquid is inert such that the at least one liquid is a media for the dissolution of one of the gases into another of the gases or for the reaction of the gases with each other whereby the gas forms microbubbles upon exposure to the lower pressure of the chamber.

11. The mixing apparatus as claimed in claim 10 wherein the Prandtl layer pump comprises a plurality of discs and a catalyst reactive with at least one of the gas and the liquid is applied to at least a portion of one of the discs.

12. The mixing apparatus as claimed in claim 10 further comprising a catalyst reactive with at least one of the gas and the liquid is housed in the chamber.

13. The mixing apparatus as claimed in claim 10 further comprising a passageway in flow communication with a source of ozone whereby the at least one gas comprises ozone and the at least one liquid comprises water and the mixing apparatus is used in the treatment of water.

14. The mixing apparatus as claimed in claim 10 further comprising a catalyst reactive with at least one of the at least one gas and the at least one liquid.

15. A mixing apparatus comprising:
   (a) a Prandtl layer means having a housing and disc means rotatably mounted within the housing;
   (b) passageway means for introducing at least one gas and at least one liquid to the housing;
   (c) chamber means for rapidly depressurizing the has/liquid mixture whereby microbubbles are produced; and,
   (d) a passageway in flow communication with a source of at least two gases whereby at least two gasses are introduced into the housing and the at least one liquid is inert such that the at least one liquid is a media for the dissolution of one of the gases into another of the gases or for the reaction of the gases with each other.

16. The mixing apparatus as claimed in claim 15 wherein the Prandtl layer means includes a plurality of discs and a catalyst reactive with at least one of the gas and the liquid is applied to at least a portion of one of the discs.

17. The mixing apparatus as claimed in claim 15 wherein a catalyst reactive with at least one of the gas and the liquid is housed in the means for rapidly depressurizing the gas/liquid mixture.

18. The mixing apparatus as claimed in claim 15 further comprising a passageway in flow communication with a source of ozone whereby the at least one gas comprises ozone and the at least one liquid comprises water and the mixing apparatus is used in the treatment of water.

19. The mixing apparatus as claimed in claim 15 wherein the Prandtl layer means is driven by a motor.

20. The mixing apparatus as claimed in claim 15 wherein the Prandtl layer means is driven by the fluid flowing through the Prandtl layer means.

* * * * *